US005941866A

United States Patent [19]

Niedospial, Jr.

[11] Patent Number: 5,941,866

[45] Date of Patent: Aug. 24, 1999

[54] MEANS TO MAINTAIN CONFIGURATION OF FLEXIBLE MEDICAL CONTAINER

[75] Inventor: John J. Niedospial, Jr., Burlington, N.J.

[73] Assignee: Bracco Research USA, Princeton, N.J.

[21] Appl. No.: 08/900,739

[22] Filed: Jul. 25, 1997

[51] Int. Cl.[6] ...................................................... A61M 5/00

[52] U.S. Cl. ........................... 604/408; 604/403; 604/411

[58] Field of Search .................................... 604/317, 403, 604/408, 409, 411, 415, 905; 383/219, 121, 121.1, 63; 222/92, 95

[56] References Cited

U.S. PATENT DOCUMENTS

| | | | |
|---|---|---|---|
| Re. 32,065 | 1/1986 | Ralston et al. . | |
| 1,901,069 | 3/1933 | Williams . | |
| 2,596,592 | 5/1952 | Parker . | |
| 2,891,700 | 6/1959 | Maynard . | |
| 4,088,166 | 5/1978 | Miller . | |
| 4,152,184 | 5/1979 | Bacehowski . | |
| 4,892,537 | 1/1990 | Carmen et al. . | |
| 4,976,707 | 12/1990 | Bodicky et al. . | |
| 5,024,344 | 6/1991 | Paula | 383/119 |
| 5,088,994 | 2/1992 | Porat . | |
| 5,129,894 | 7/1992 | Sommermeyer et al. | 604/408 |
| 5,259,844 | 11/1993 | Bilstade et al. | 604/403 |
| 5,391,163 | 2/1995 | Christine et al. | 604/408 |
| 5,423,794 | 6/1995 | Adolf et al. . | |
| 5,496,299 | 3/1996 | Felix et al. | 604/319 |

*Primary Examiner*—Ronald Stright
*Assistant Examiner*—David J. Cho
*Attorney, Agent, or Firm*—Imre Balogh

[57] ABSTRACT

A unitary, flexible container, for containment and delivery of medical fluids, having:

a) first and second polymeric sheets superimposed and sealed together at their periphery defining an interior reservoir, the container having a top portion, a mid portion and a bottom portion; the bottom portion terminates in a first angle and a second angle of from about 5° to about 45° each from the center of the bottom portion to a horizontal plane crossing the center of the bottom portion;

b) an access member integral with the unitary, flexible container located at the center of the bottom portion allowing filling the flexible container with medical fluids and access to the medical fluids for delivery to a patient; and c) at least one oval shaped rigid reinforcing disc positioned in the mid portion of the interior reservoir to prevent collapse of the walls of the container on each other causing hold up of droplets.

11 Claims, 1 Drawing Sheet

MEANS TO MAINTAIN CONFIGURATION OF FLEXIBLE MEDICAL CONTAINER

BACKGROUND OF THE INVENTION

1. Field of the Invention

This invention relates to flexible plastic containers, such as bags, pouches and bottles, for the containment and delivery of fluids. More particularly the invention relates to flexible plastic containers for the containment and delivery of parenteral solutions including diagnostic contrast media, nutrients and drug formulations.

2. Reported Developments

Prior to the discovery and development of polymeric materials, parenteral liquids have been supplied to hospitals exclusively in glass bottles. The disadvantages of glass bottles, such as cost, shipping, storage and disposal, prompted the prior art to provide flexible, sterilizable containers in the forms of bags and bottles for the containment and delivery of parenteral solutions, such as diagnostic contrast media, nutritional and drug formulations. Such containers typically comprise: a flexible plastic sheet formed into a pouch, bag or bottle shape filled with a solution inside therein in a sterile environment; and one or more ports to fill and/or access the solution. Flexible tubing is also provided one end of which is connectable to a port on the container, and the other end connectable to a syringe or catheter pre-inserted into the site of delivery on the patient. Control means are also usually included with the tubing, such as valves and clamps for initiating, controlling and terminating the flow of the liquid to the delivery site. The container, tubing and control means are sterile packaged ready for use.

One of the requirements to be satisfied in flexible containers for delivering parenteral solutions to patients is that by their construction and design they deliver their total contents in a uniform, steady manner and without retaining liquid drops on their walls. By meeting such requirement the medical practitioner can determine the amount of parenteral solution delivered from the container to the patient. The prior art has addressed this requirement, as shown for example in U.S. Pat. No. 4,892,537, which discloses a bag having substantially parallel major sides or edges and converging minor sides which meet at a point forming an obtuse angle of at least 110°. The converging edges are designed to guide the filled bag contents in a substantially unobstructed manner in a funnel-like fashion to an exit port.

U.S. Pat. No. 4,088,166 also addresses the problem of incomplete and non-uniform collapse of parenteral solution containers. The incomplete collapse is attributed to the stiffness of the thin-walled polypropylene container which tends to resist collapse to such a degree that the moderate suction pressure exerted on the container by weight of the parenteral solution is insufficient to cause its complete collapse. The non-uniform collapse, on the other hand, is attributed to the observed facts that on some occasions, the bags collapse along the long axis of their cross section, while on other occasions they tend to collapse along both the short axis of the cross-section as well as the long axis. As a result, the medical practitioners cannot determine exactly how much parenteral solution has been delivered out from the container. In order to solve the problem of incomplete and non-uniform delivery, the patentee incorporates gusset portions in the body portion of the container adjacent the shoulder portion. The gusset portions include lines of flexing weakness to facilitate the collapse of the container adjacent the shoulder portion as the contents thereof are withdrawn. The gussets said to facilitate both the lateral and longitudinal collapse of the container as it is emptied.

Medical practitioners have also observed fluid "hold up", i.e., when drops of parenteral solutions tend to remain on the internal walls of the flexible container as the solution is being delivered to the site of administration. The moderate suction pressure exerted on the walls of the container is insufficient to overcome the force existing between the drops of liquid and the walls of the container. Often, as the container is being drained, the emptied portion of the parallel walls adhere to each other further trapping drops of the liquid. As a consequence, the prescribed amount of parenteral solution is not delivered to the patient. Such delivery, especially in traumatic circumstances where a precise amount of a drug must be delivered into the patient, can make the difference between life and death of the patient.

The present invention addresses the problems associated with the lack of complete delivery of content, such as incomplete and non-uniform collapse of the container during administration of the parenteral solution, and hold up of drops of the solution on the walls of the container. The present invention provides means by which the parallel walls of the container are spaced apart from each other by having at least one elongated oval shaped reinforcing means, containing ribs therein, incorporated in the container.

SUMMARY OF THE INVENTION

The present invention is directed to a flexible, unitary plastic container, such as a bag, pouch or bottle, for the containment and delivery of parenteral solutions, such as diagnostic contrast media, nutrients and drug formulations to a patient in need of such parenteral solutions.

The flexible plastic container may be of any configuration, such as, square, rectangular, round, oval, hexagonal or octagonal. Typically, it is a generally rectangular configuration which will be described hereunder.

The container comprises:

a) first and second flexible plastic sheets having a generally rectangular configuration superimposed and sealed together at their periphery to form a pouch defining an interior, said pouch having a top and a bottom portion; said bottom portion terminates in a first angle and a second angle of from about 5° to about 45°, preferably of from about 10° to about 30°, and most preferable from 10° to 20° from the center of said bottom portion and relative to a horizontal plane crossing the center of said bottom portion to direct and facilitate the flow of content of the solution contained in the pouch towards an access port;

b) an access member integral with said pouch located at the center of the bottom portion of said pouch for allowing filling of the container with a parenteral solution and access thereto for its delivery, said access member comprising:

1) an access port located below the bottom portion of said pouch where said first angle and said second angle meet; and 2) a flexible tubing one end of which is integral with said access port and the other end of which is removably covered with a cap; said flexible tubing may be equipped with a one way luer slip lock assembly with a vent for controlling the delivery of the parenteral solution from the container; and c) an oval shaped reinforcing means containing ribs therein positioned horizontally in the pouch, preferably at the center thereof.

The one-way luer slip stopcock assembly with vent may be positioned at the open end just below the removable cap, or it may be positioned next to and adjacent to the port.

Preferably the top portion at the periphery of the container comprises at least one hole for suspending the container when it is in use for delivering the content thereof to the delivery site.

Additional features and advantages of the present invention will be apparent from the drawings and of the detailed description.

DETAILED DESCRIPTION OF THE INVENTION

Figure 1:
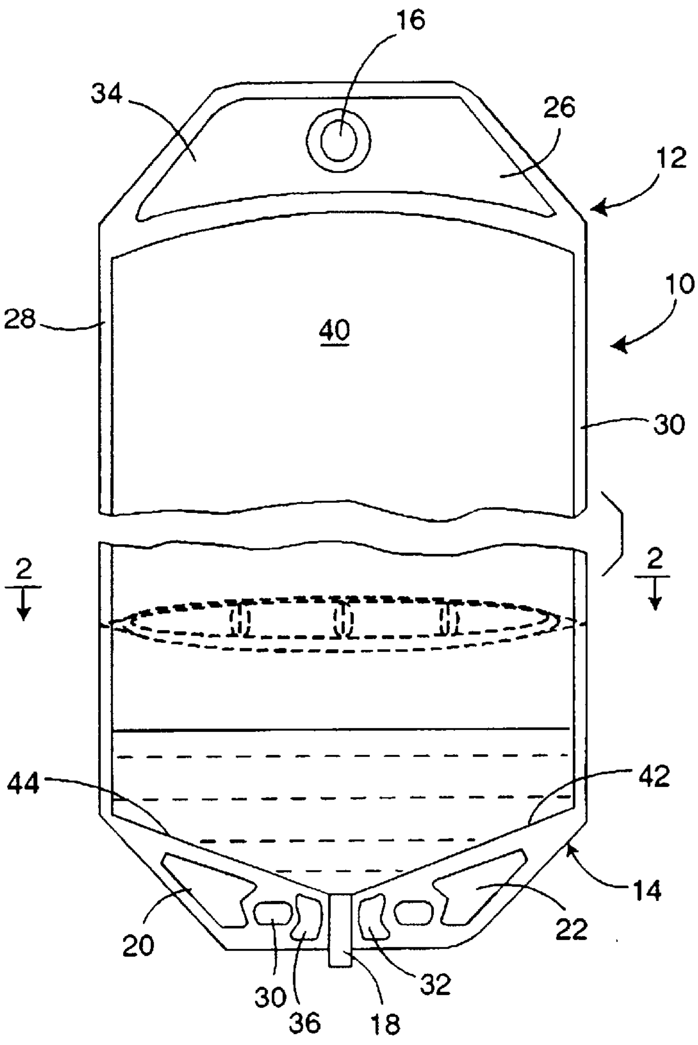
FIG. 1 is a plan view of the flexible container in accordance with the present invention showing an access member or port which serves for both filing the container and for delivering its content.

It was surprisingly discovered that if the inside wall of the first sheet and the second sheet forming the container 10 is kept apart from each other, fluid hold up in the form of drops adhering to the inside walls can be reduced or eliminated.

The present invention provides a flexible plastic container, in the shape of a bag or pouch, for the containment and delivery of diagnostic contrast media, nutrients and drug formulations. In the drawings where the reference character 10 in FIG. 1 indicates the container which, in a preferred embodiment, is a pouch-like device, comprising two superimposed sheets of suitable length and width made of flexible or pliable materials, such as polymeric materials including polyethylene, polypropylene, and preferably thermoplastic materials. The superimposed sheets forming the pouch-like container are preferably made of transparent materials so as to allow observation of the amount of its content prior to and subsequent to the fling sterilization operation and delivery thereof to the patient. Each of the superimposed transparent sheets is preferably formed of multilayers of laminated thin films at least one of which constitutes a barrier which is impervious to atmospheric gases, moisture and bacteria. The superimposed sheets are preferably mono or multilayer flat welded to each other so as to form the pouch whose volume is zero before it is filled with a parenteral solution. When the pouch is filled or partially filled, it assumes the shape of a small cushion. The superimposed sheets are joined together along marginal areas 28 and 30 as shown in FIG. 1.

Reference is now being made to the parts of the flexible container of the present invention using reference characters.

FIG. 1 shows the flexible container 10 sealed around its periphery 28 and 30 forming a reservoir or pouch for the containment of diagnostic contrast media, nutrients and drug formulations. The container has a top portion 12 and a bottom portion 14. Top portion 12 comprises marginal areas 34 and 26 sealed around their periphery and hole 16 at the center thereof for suspending the container when it is in use for delivering its content 40 to a delivery site.

The bottom portion 14 of container 10, defined by seal areas 44 and 42, terminates in first angle and second angle from the center thereof and relative to a horizontal plane crossing the center to direct and facilitate the flow of content contained in the container towards an access port. First and second angles are of from about 5° to about 45°, preferably from 10° to 30° and most preferably form 10 to 20°.

An access member or port 18 located at the center of the bottom portion of container 10 is sealed between the first sheet and second sheet of the container comprising a top, liquid-contacting portion and a bottom portion to which a flexible tubing, i.e., intravenous (IV) line may be fixedly attached by heat sealing or by any other means. Access member or port 18 serves for both the filing and for the delivery of the parenteral liquid. It is important that top portion of access member 18 is located below a horizontal plane crossing the center seal areas 44 and 42 so that all the liquid content of the container can be drained into flexible tubing of an IV line.

The bottom portion 14 further comprises marginal areas 20, 22, 30, 32 and 38 sealed around their periphery. These areas serve as reinforcements of the bottom portion 14.

Figure 2:
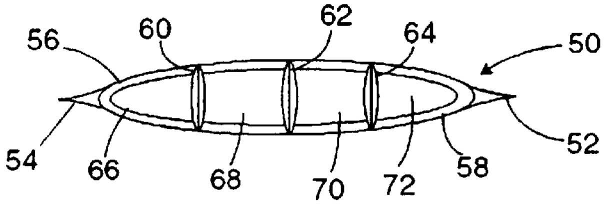
FIG. 2 is a cross-section showing a reinforcing means, containing ribs therein, taken along the line 2—2 of FIG. 1.

A generally oval shaped reinforcing member or disc 50 is located inside the reservoir 40 approximately at the center thereof and attached by heat sealing or by other means to the inside wall of the reservoir as shown by seal lines 54 and 52 in FIG. 2.

Reinforcing member 50 is constructed from rigid polymeric material and comprises an oval shaped diskette narrowing at 56 and 58 towards the periphery 28 and 30, respectively, of reservoir 40; and ribs 60 , 62 and 64 spanning the oval shaped diskette to insure that the oval shape of the diskette will not be deformed by the weight of the content of the reservoir. Ribs 60, 62 and 64 are spaced apart and along with the diskette define openings or holes allowing the liquid content to move freely towards the access member or port 18. While FIG. 2 shows three ribs 60, 62 and 64, it is to be noted that more than three ribs may be used to reinforce the diskette. Alternatively, if the diskette is sufficiently rigid to maintain its oval shape under the weight of the content of the reservoir, the diskette may be without the reinforcing ribs. It is also to be noted that more than one diskette maybe used to keep the inside walls of the reservoir apart from each other so that no liquid droplets will be trapped between the walls when the content is being delivered.

Materials Of Construction

The flexible container of the present invention is made of known polymeric materials having properties which make them suitable for sterile delivery of parenteral liquids. The sheets for forming the walls of the container are monolayer, preferably multilayer, sheets and characterized by heat resistance, gloss, strength, flexibility, and chemical inertness. Preferably the sheets are transparent or at least translucent enabling visual inspection of the contents at all times during delivery of content from the container to the patient. The container must be sterilizable by dry heat, steam heat, irradiation (gamma), along with its content. At least one layer of the sheet provides a barrier to atmospheric gases and to steam. Preferably, the internal surface of the pouch in contact with the parenteral solution should be impervious to gases and steam The interior layer in contact with the parenteral solution must not contain any toxic agents or even plasticizers which could leach out and contaminate the solution. The sheet may be made, for example, from polyvinyl chloride sandwiched between two polyethylene or polyvinylacetate layers. The polyvinyl chloride constitutes the impervious barrier. Further layers may be added to the face or back of the sheet, if desired, such as a polyolefin, preferably, polyethylene. Polyvinyl chloride is also suitable for the construction of the sheet and is well-accepted by the prior art for use in containers for medical fluid collection and delivery. Typical properties of polyvinyl chloride films include: a thickness of about 380 micron; a tensile strength of about 240 kg/cm$^2$; a moisture vapor transmission rate of about 14–20 (g/m$^2$/day at 38° C., 100% RH); and an oxygen barrier of 650 (cc/m$^2$/day at 23° C., 0% RH, bar. CRYOVAC® sterilizable medical films (W.R. Grace and Co.) are especially suitable to construct the sheets used in the present invention. The films may comprise a polyethylene layer sandwiched between polyester outer layers sealed together by a modified propylene copolymer. Typical properties of the film include: a thickness of about 190 micron; a tensile strength of about 250 kg/cm$^2$; a moisture vapor transmission rate of 5 (g/m$^2$/day at 38° C., 100% RH); and an oxygen barrier of about 1500 (cc/m$^2$/day at 23° C., 0% RH, bar).

Other preferred polymeric films or sheets for constructing the flexible container of the present invention include: copolyester ether monolayer or multilayer films, manufactured from such as polycyclohexanedimethylcyclohexane dicarboxylate elastomer made by Eastman Chem. Co.; and ethyl vinyl acetate made by Stedim, Inc. It is important that the fluid contacting layer of the multilayer sheet contain no plasticizer which may contaminate the fluid content of the container. Preferably, no plasticizer should be used at all on any of the multilayers to form a flexible container of the present invention.

Access member or port as well as the oval shaped reinforcing disc and ribs may be made of polyvinyl chloride which are sold commercially for use in medical devices. Other materials may also be used, such as CRYOVAC® Port Tubing (W.R. Grace & Co.) which comprise three concentric layers of polymeric materials: a polyolefin layer is sandwiched between an outer layer of modified propylene copolymer and an inner layer of ethylene vinyl acetate or polyvinyl chloride.

Process of Making the Container

The flexible plastic container in the form of a bag, pouch or bottle is made of two rectangular sheets of polymeric materials flat welded together on four sides so as to define between the two sheets and the four welded sides a reservoir. The container typically has an internal volume capacity of from about 50 to about 1,000 ml when it is filled with a medical fluid, such as a parenteral solution. The access member or port 18 is sealed by the same welding process used to seal the two superimposed layers of sheets together at the bottom center of the container 10.

Chronologically the process of making the container comprises the steps of:

a) pre-making the desired size of the reinforcing disc with or without the ribs by a method known in the art, such as blow molding;

b) cutting the desired size of rectangular sheets;

c) heat welding the reinforcing disc to one of the rectangular sheets followed by heat welding the other rectangular sheet to the disc; and d) welding together the rectangular sheets on four sides and simultaneously welding the access member or port into the bottom center portion of the container. Upon completion of the welding process the container is filled with the desired medical fluid and capped.

Alternatively, the container may be sealed by heat welding at its four edges except at its bottom center portion and filled with the desired medical fluid prior to sealing access member or port between the superimposed sheets. With either process, the container of the present invention, when filled with the desired medical fluid, provides for instant delivery requiring no assembly of the container and access member.

In the process of delivering the medical fluid to a patient, the container 10 is suspended via hole 16, the cap is removed and an IV line or tubing is engaged to access member 18. In the IV line one way luer slip stopcock assembly is turned to open position thereby starting the flow of medical fluid from the container through the tubing to the site of delivery on the patient. If discontinuation of fluid flow is desired, the one-way luer stopcock assembly is turned to the stop position.

In laboratory experiments the filled container of the present invention was found to deliver its content at a steady rate without collapse of the walls and without hold up of droplets on the inside of the walls.

Various modifications of the present invention disclosed will become apparent. This invention is intended to include such modifications to be limited only by the scope of the claims.

What is claimed is:

1. A unitary, flexible container made of a polymeric material for the containment and delivery of medical fluids comprising:

a) first and second polymeric sheets superimposed and sealed together at their periphery defining an interior reservoir, said container having a top portion, a mid portion and a bottom portion;

said bottom portion terminates in a first angle and a second angle of from about 5° to about 45° each from the center thereof and relative to a horizontal plane crossing the center of said bottom portion;

b) an access member integral with said container located at the center of said bottom portion allowing filling of the container with a medical fluid and access thereto for delivery to a patient; and c) at least one oval shaped rigid reinforcing disc positioned in said mid portion of the interior reservoir.

2. The unitary, flexible container of claim 1 wherein said rigid reinforcing disc contains at least one rigid rib therein.

3. The unitary, flexible container of claim 1 wherein said polymeric sheets sealed together at their periphery are of rectangular configuration.

4. The unitary, flexible container of claim 1 wherein said bottom portion terminates in the first and the second angle of from about 10° to about 30° each from the center thereof and relative to the horizontal plane crossing the center of said bottom portion.

5. The unitary, flexible container of claim 1 wherein said bottom portion terminates in the first and the second angle of from about 10° to about 20° each from the center thereof and relative to the horizontal plane crossing the center of said bottom portion.

6. The unitary, flexible container of claim 1 wherein said container further comprises at its top portion a heat welded periphery housing a hole therein for suspending said container during the delivery process.

7. The unitary, flexible container of claim 1 wherein said first and second polymeric sheets are made of polyvinylidene chloride sandwiched between two layers of polyethylene or polyvinylacetate.

8. The unitary, flexible container of claim 1 wherein said first and second polymeric sheets are made of polyvinyl chloride.

9. The unitary, flexible container of claim 1 wherein said first and second polymeric sheets are made of a polyethylene layer sandwiched between polyester outer layers sealed together by a propylene copolymer.

10. The unitary, flexible container of claim 1 wherein said first and second polymeric sheets are made of polycyclohexanedimethylcyclohexane dicarboxylate.

11. The unitary, flexible container of claim 1 wherein said first and second polymeric sheets are made of ethyl vinyl acetate.

* * * * *